US007001757B1

United States Patent
Rosamund et al.

(10) Patent No.: US 7,001,757 B1
(45) Date of Patent: Feb. 21, 2006

(54) PROTEIN

(75) Inventors: John David Charles Rosamund, Waltham, MA (US); Norbert Friedemann Schnell, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/069,062

(22) PCT Filed: Aug. 15, 2000

(86) PCT No.: PCT/GB00/03100

§ 371 (c)(1),
(2), (4) Date: Feb. 21, 2002

(87) PCT Pub. No.: WO01/14533

PCT Pub. Date: Mar. 1, 2001

(30) Foreign Application Priority Data

Aug. 21, 1999 (GB) .................................. 9919766

(51) Int. Cl.
*C12N 1/14* (2006.01)
*C12Q 1/68* (2006.01)
*C12P 21/06* (2006.01)
*C07H 21/04* (2006.01)
*A61K 39/00* (2006.01)

(52) U.S. Cl. .................. 435/254.22; 435/6; 435/252.3; 435/254.1; 424/184.1; 424/185.1; 424/274.1; 514/2; 514/15; 536/23.1; 536/23.7

(58) Field of Classification Search ............. 424/184.1, 424/185.1, 274.1; 514/2, 15; 536/23.1, 536/23.2, 23.7; 435/69.1, 193.1, 252.3, 254.1, 435/320.1, 254.22

See application file for complete search history.

(56) References Cited

U.S. PATENT DOCUMENTS 5,885,815 A    3/1999   Kaufmann et al.

OTHER PUBLICATIONS

Bowie et al. Science, vol. 247: 1990; p. 1306; p. 1308.*
Houghten et al. (Vaccines, 1986, Edited by Fred Brown: Cold Spring Harbor Laboratory).*
Accession No.: M63648.*
Tsay, et al., "Cloning and characterization of ERG8, an essential gene of *Saccharomyces cerevisiae* that encodes phosphomevalonate kinase" Molecular and Cellular Biology, vol. 11, No. 2, Feb. 1991, pp. 620-5631, XP000981936.
Lees et al., "Biochemistry and molecular biology of sterol synthesis in *Saccharomyces cerevisiae*", Critical Reviews in Biochemistry and Molecular Biology, vol. 34, No. 1, Jan. 1999, pp. 33-47, XP000981947.
Hartman et al., "Inhibitors of ergosterol biosynthesis as antifungal agents", Current Pharmaceutical Design, vol., 3, No. 2, Apr. 1997, pp. 177-208, XP000981960.
Jensen-Pergakes et al., "Sequencing disruption and characterization of the *Candida albicans* sterol methyltransferase (ERG6) gene: drug susceptibility studies in erg6 mutants", Antimicrobial Agents and Chemotherapy, vol. 42, No. 5, May 1998, pp. 1160-1167.
Kelly et al., "Cloning and characterization of the 2,3-oxidosqualene cyclase-coding gene of *Candida albicans*", GENE, vol. 87, No. 2, Mar. 1990, pp. 177-183, XP992160270.
Mannarelli et al., "Rapid identification of *Candida albicans* and other human pathogenic yeasts by using short oligonucleotides in PCR", Journal of Clinical Microbiology, vol. 36, No. 6, Jun. 1998, pp. 1634-1641, XP002160271.

* cited by examiner

*Primary Examiner*—Lynette R. F. Smith
*Assistant Examiner*—Padma Baskar
(74) *Attorney, Agent, or Firm*—Morgan Lewis & Bockius LLP

(57) ABSTRACT

This invention relates to polynucleotides, polypeptides encoded by these polynucleotides, to the production of such polynucleotides and polypeptides, and to the uses of such polynucleotides and polypeptides. More specifically, the invention relates to the phosphomevalonate kinase (PMK) gene (ERG8 gene) from *Candida Albicans* (*C. albicans*), to methods for its expression yielding phosphomevalonate kinase protein, to hybrid organisms for use in such expression methods, to methods for purification of the protein, to methods and tools for diagnosing *C. albicans* infection and to assays for identifying inhibitors of the enzyme which inhibitors have potential as anti-fungal agents.

4 Claims, 1 Drawing Sheet

```
GTGGAAAAAAAAGACAGAACAGTAGATTCCAACTTCAGAATATTCATTCAGATCTGAACATTT
CTTTTTCTCCGATCATCAATTGGCAATGTCAAAAGCATTTAGTGCACCTGGAAAAGCATTTCT
TGCTGGTGGATATTTGGTTCTTGAGCCAATTTATGATGCTTATGTGACAGCATTGTCATCACG
AATGCATGCAGTTATAACACCAAAAGGAACCAGTTTGAAAGAATCTAGAATCAAAATTTCTTC
ACCCCAATTTGCAAACGGAGAATGGGAATATCACATATCATCAAATACAGAGAAGCCCAGAGA
AGTTCAGTCACGCATAAATCCATTTTAGAGGCAACTATATTCATCGTTTTAGCTTATATTCA
ACCGACCGAAGCATTTGATCTTGAAATCATCATTTACTCAGACCCTGGATATCATTCACAAGA
AGATACTGAAACCAAGACATCCTCGAATGGAGAAAAAACATTTCTTTACCATTCTCGTGCCAT
TACCGAAGTGGAAAAGACCGGATTAGGTTCATCGGCAGGATTAGTGTCAGTTGTTGCCACAAG
TTTATTATCCCATTTTATCCCCAATGTTATCAGTACGAATAAAGATATTTTGCACAACGTTGC
ACAGATTGCACATTGTTATGCCCAAAAAAGATAGGATCTGGGTTTGATGTTGCAACTGCAAT
TTATGGTCTGATTGTATATAGAAGATTTCAGCCAGCTTTGATAAATGACGTGTTTCAGGTTCT
AGAAAGTGATCCTGAGAAGTTCCCCACAGAGTTGAAAAAATTGATTGAAAGTAACTGGGAATT
CAAACATGAAAGATGTACATTACCATACGGAATCAAGTTATTAATGGGTGACGTCAAGGGTGG
CTCAGAAACACCCAAATTGGTATCACGAGTACTCCAATGGAAAAAGGAAAAGCCAGAAGAAAG
CTCTGTTGTGTATGACCAGCTTAATAGTGCCAATTTACAGTTTATGAAGGAATTGAGGGAAAT
GCGTGAAAAATACGACTCAGACCCAGAGACTTATATTAAAGAGTTAGATCATTCTGTTGAGCC
TTTGACTGTTGCGATTAAGAACATCAGAAAAGGGTTACAAGCATTAACACAAAAATCAGAGGT
TCCAATTGAACCTGATGTCCAAACCCAGTTGTTGGACCGTTGTCAAGAGATTCCTGGTTGTGT
TGGTGGTGTGGTTCCAGGTGCTGGTGGATACGATGCAATAGCTGTATTAGTGTTGGAAAATCA
AGTGGGAAATTTTAAGCAGAAAACTCTTGAAAATCCAGATTATTTTCATAATGTTTACTGGGT
TGATTTGGAAGAGCAAACAGAAGGTGTACTTGAAGAAAAACCAGAAGACTATATAGGTTTATA
AAATATCACTGGGATATGTCTACAAGGTGTTTTCGATTAGAGTTTTTGATCCCCATTTTAACA
TATTTTACTTCAATCTTACACTTTATCCTTTTAAGTAGGTATGTGTAGGGAAAGAGCCTGATC
TTCATAAACCGTTGCAAACTAATTGATTATATTTTCTATTGTAAATTTCATATGCAGGAAATA
GCTTATTCGACAAATTATTTATTTTCGTCTCGTTCTGGTCCAAGTACCCCAGAGACGAAATAA
CTGACAACACGCAGGGCTGGGTTGGCATTTTCGTCACACGATTATTATTAATGGTAACAAAAA
AAGGGGRKATGCCCGTGGTCGATACACAAATATTTATGATATACTTTCCATATTTTTTTTT
```

PROTEIN

FIELD OF INVENTION

This invention relates to newly identified polynucleotides, polypeptides encoded by these polynucleotides, to the production of such polynucleotides and polypeptides, and to the uses of such polynucleotides and polypeptides. More specifically, the invention relates to the phosphomevalonate kinase (PMK) gene (ERG8 gene) from Candida albicans (C. albicans), to methods for its expression yielding phosphomevalonate kinase protein, to novel hybrid organisms for use in such expression methods, to methods for purification of the protein, to methods and tools for diagnosing C. albicans infection and to assays for identifying inhibitors of the enzyme which inhibitors have potential as anti-fungal agents.

BACKGROUND OF INVENTION

C. albicans is an important human fungal pathogen and the most prominent target organism for antifungal research. PMK is an enzyme required for the biosynthesis of isoprene subunits that are used as precursors in the synthesis of sterols, dolichols and ubiquinones. As PMK is an essential biosynthetic enzyme, inhibitors of PMK should find use as antifungal agents. All species synthesise a protein with PMK activity however, across species the enzymes differ considerably in their amino acid sequence. Because of selectivity problems (for example fungal versus human) it is extremely important to optimise potential inhibitors specifically against the fungal target enzymes (i.e. C. albicans or Aspergillus fumigatus) and not against the human enzyme. Such cross-fungal-species inhibitors possess broad specificity. Alternatively, it may be desirable to use an inhibitor which is more selective, for example, one that inhibits C. albicans PMK but not a homologous but non-identical fungal PMK protein such as from Saccharomyces cerevisiae (S. cerevisiae).

In view of the increased incidence of fungal resistance to existing anti-fungal agents and fuelled by the growing number of fungal infections particularly in people with immunodeficiency disorders, organ transplants and cancer, there is a need for new means of identifying potential anti-fungal agents.

SUMMARY OF INVENTION

We have now successfully cloned the ERG8 gene from C. albicans (hereinafter referred to as ERG8 gene) and determined its full length nucleotide sequence and corresponding (PMK) polypeptide sequence (hereinafter referred to as ERG8 protein) as set out in FIG. 1 and SEQ ID No. 7 of this application respectively. The coding DNA sequence (SEQ ID NO. 6) of the C. albicans ERG8 gene isolated is 1299 nucleotides in length and the corresponding protein sequence is 433 amino acids in length (SEQ ID NO. 7). The protein exhibits approximately 45% homology with the corresponding protein from S. cerevisiae and only about 10% homology to that of the human protein equivalent. Homology as used herein, takes the definition known to and routinely used by molecular biologists. It refers to the sequence identity between two sequences as assessed by best-fit computer alignment analysis using suitable software such as Blast, Blast2, NCBI Blast2, WashU Blast2, FastA, Fasta3 and PILEUP, using a scoring matrix such as Blosum 62. Such software packages endeavour to closely approximate the "gold-standard" alignment algorithm of Smith-Waterman. Thus, the preferred software/search engine programme for use in assessing the percent identity or similarity, i.e how two primary polypeptide sequences line up is Smith-Waterman. Identity refers to direct matches, similarity allows for conservative substitutions.

BRIEF DESCRIPTION OF THE DRAWINGS

FIG. 1 contains a polynucleotide sequence comprising the C. albicans ERG8 gene (SEQ ID No. 5).

DETAILED DESCRIPTION OF THE INVENTION

According to a first aspect of the invention there is provided an isolated or purified polypeptide which is ERG8 protein, as well as variants thereof. The preferred polypeptide sequence is that as set out in SEQ ID NO. 7. The complete C. albicans phosphomevalonate kinase enzyme polypeptide has the amino acid sequence as depicted in SEQ ID No. 7 herein. The polypeptides of the present invention include the polypeptide of SEQ ID No. 7 as well as polypeptides which have in increasing order of preference, at least 75%, 80%, 85%, 90%, 95%, 96%, 97%, 98%, and 99% identity to the polypeptide whose amino acid sequence is depicted in SEQ ID NO. 7.

As used herein, the term "isolated" refers to molecules, either nucleic acid or amino acid sequences, that are removed from their natural environment and purified or separated from at least one other component with which they are naturally associated. Also encompassed by this term are molecules that are artificially synthesised and purified away from their synthesis materials. Thus, a polynucleotide is said to be isolated when it is substantially separated from other contaminant polynucleotides or nucleotides.

Although the natural polypeptide of SEQ ID NO. 7 and a variant polypeptide may only possess for example 80% identity, they are actually likely to possess a higher degree of similarity, depending on the number of dissimilar codons that are conservative changes. Similarity between two sequences includes direct matches as well as conserved amino acid substitutes which possess similar structural or chemical properties, e.g. similar charge. Examples of conservative changes (conserved amino acid substitutes) are inter alia: alanine to glycine, isoleucine, valine or leucine; tyrosine to phenylalanine or tryptophan; and lysine to arginine or histidine.

Suitable conservative substitutions of amino acids are known to those of skill in this art and may be made without altering the biological activity of the resulting polypeptide, regardless of the chosen method of synthesis. The phrase "conservative substitution" includes the use of a chemically derivatized residue in place of a non-derivatized residue provided that such polypeptide displays the desired binding activity. D-isomers as well as other known derivatives may also be substituted for the naturally occurring amino acids. See, e.g., U.S. Pat. No. 5,652,369, Amino Acid Derivatives, issued Jul. 29, 1997. Substitutions are preferably, although not exclusively, made in accordance with those set forth in TABLE 1 as follows:

TABLE 1

| Original residue | Example conservative substitution |
|---|---|
| Ala (A) | Gly; Ser; Val; Leu; Ile; Pro |
| Arg (R) | Lys; His; Gln; Asn |
| Asn (N) | Gln; His; Lys; Arg |
| Asp (D) | Glu |
| Cys (C) | Ser |
| Gln (Q) | Asn |
| Glu (E) | Asp |

TABLE 1-continued

| Original residue | Example conservative substitution |
| --- | --- |
| Gly (G) | Ala; Pro |
| His (H) | Asn; Gln; Arg; Lys |
| Ile (I) | Leu; Val; Met; Ala; Phe |
| Leu (L) | Ile; Val; Met; Ala; Phe |
| Lys (K) | Arg; Gln; His; Asn |
| Met (M) | Leu; Tyr; Ile; Phe |
| Phe (F) | Met; Leu; Tyr; Val; Ile; Ala |
| Pro (P) | Ala; Gly |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala |

The nucleotide sequences of the present invention may also be engineered in order to alter a coding sequence for a variety of reasons, including but not limited to, alterations which modify the cloning, processing and/or expression of the gene product. For example, mutations may be introduced using techniques which are well known in the art, eg, site-directed directed mutagenesis to insert new restriction sites, to alter glycosylation patterns, to change codon preference, etc.

Included within the scope of the present invention are alleles of the ERG8 molecule of the present invention. As used herein, an "allele" or "allelic sequence" is an alternative form of the kinase molecule described herein. Alleles result from nucleic acid mutations and mRNA splice-variants which produce polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Thus, according to a preferred embodiment there is provided an isolated polypeptide comprising the sequence depicted in SEQ ID No. 7 or a sequence possessing at least 80% similarity thereto. More preferred embodiments are those that have in increasing order of preference at least 85, 90, 95, 96, 97, 98 and 99% similarity to the sequence depicted in SEQ ID No. 7. Functional biologically active variants are preferred.

Fragments of such polypeptides comprising at least 15, preferably at least 30 and more preferably at least 50 contiguous amino acids are also encompassed by the present invention. Such fragments may be used as intermediates to generate longer polypeptide fragments including preferably, the full-length polypeptide sequence as depicted in SEQ ID No. 7, or a functional variant thereof. Such polypeptide fragments may also be used to raise antibodies against or specific for parts of the ERG8 protein.

The invention also relates to variant polypeptide sequences encoded by nucleic acid capable of hybridising with nucleic acid coding for the natural polypeptide (SEQ ID No. 6, or its complementary antisense strand)(or would do so but for the degeneracy of the genetic code), for example under stringent conditions (such as at 35° C. to 65° C. in a salt solution of approximately 0.9M). Such hybridisable polynucleotides are also part of the invention. The present invention particularly relates to polynucleotides which hybridise to the ERG8 polynucleotide sequence depicted in SEQ ID NO. 6, its complementary sequence, or fragment thereof, under stringent conditions. As used herein, stringent conditions are those conditions which enable sequences that possess at least 80%, preferably at least 90% and more preferably at least 95% sequence identity to hybridise together. Thus, nucleic acids which can selectively hybridise to the nucleic acid of SEQ ID No. 6, or the complementary antisense strand thereof, include nucleic acids which have at least 80%, preferably at least 90%, more preferably at least 95%, still more preferably at least 98% sequence identity and most preferably 100%, over at least a portion of the nucleic acid encoding the ERG8 gene disclosed herein. Selectively hybridise means that the molecule must be capable of specifically hybridising to the nucleic acid sequence of SEQ ID No. 6 or its complement, to the exclusion of other naturally occurring sequences. As well as full-length gene sequences, smaller nucleic acid fragments for example oligonucleotide primers which can be used to amplify the ERG8 gene using any of the well known amplification systems such as polymerase chain reaction (PCR), or fragments that can be used as diagnostic probes to identify corresponding nucleic acid sequences are also part of this invention. The invention thus includes polynucleotides of shorter length than the full length ERG8 gene sequence depicted in SEQ ID No. 6, that are capable of specifically hybridising to the nucleic acid encoding the C. albicans ERG8 gene described herein. Such polynucleotides may be at least 10 nucleotides in length, preferably at least 15, more preferably at least 20 and most preferably at least 30 nucleotides in length and may be of any size up to and including the full length ERG8 nucleotide sequence. The presence of mismatch nucleotides in the hybridisation polynucleotides is not detrimental to the utility of such polynucleotides provided that they are capable of selectively hybridising to the target ERG8 nucleotide sequence.

An example of a suitable hybridisation solution when a nucleic acid is immobilised on a nylon membrane and the probe nucleic acid is greater than 500 bases or base pairs is: 6×SSC (saline sodium citrate), 0.5% SDS (sodium dodecyl sulphate), 100 µg/ml denatured, sonicated salmon sperm DNA. The hybridisation being performed at 68° C. for at least 1 hour and the filters then washed at 68° C. in 1×SSC, or for higher stringency, 0.1×SSC/0.1% SDS.

An example of a suitable hybridisation solution when a nucleic acid is immobilised on a nylon membrane and the probe is an oligonucleotide of between 12 and 50 bases is: 3M trimethylammonium chloride (TMACl), 0.01M sodium phosphate (pH 6.8), 1 mM EDTA (pH 7.6), 0.5% SDS, 001 µg/ml denatured, sonicated salmon sperm DNA and 0.1 dried skimmed milk. The optimal hybridisation temperature (Tm) is usually chosen to be 5° C. below the Ti of the hybrid chain. Ti is the irreversible melting temperature of the hybrid formed between the probe and its target. If there are any mismatches between the probe and the target, the Tm will be lower. As a general guide, the recommended hybridisation temperature for 17-mers in 3M TMACl is 48–50° C.; for 19-mers, it is 55–57° C.; and for 20-mers, it is 58–66° C.

A suitable hybridisation protocol is described in Example 5 herein, however, operable variations to this method will be apparent to the person skilled in the art.

As used herein, the term 'variant' includes naturally occurring allelic variants as well as non-naturally occurring variants, fragments and analogs of the sequences depicted in SEQ ID NOs. 6 or 7. Such variants include C- or N-truncated variants, deletion variants, substitution variants as well as addition and insertion variants. The term 'analog' refers to proproteins which can be activated by cleavage of the proprotein portion to release the biologically active polypeptide or protein. The term 'derivative' refers to a polypeptide encoded by a chemically modified ERG8 gene, for example one wherein hydrogen has been replaced by an acyl or amino group, as well as polypeptides possessing one or more non-natural amino acids. When referring to a polypeptide or protein sequence, a functional variant is one that has retained at least some PMK enzymatic activity. The variant polypeptides of the present invention may comprise internal, but preferably, terminal flanking sequences (fusion proteins) to facilitate protein purification. Such 'additional domain' sequences (Flag sequences) may comprise for example, metal chelating peptides such as histidine-tryptophan modules (including 6-his tags) that allow purification of the polypeptide on immobilised metals, protein A domains that allow purification on immobilised immunoglobulin, or peptide domains that allow purification on immobilised antibodies specific for the peptide. Other suitable 'additional purification domains' will be known to the person skilled in the art.

According to a preferred embodiment of the invention the native ERG8 polypeptide sequence (having the sequence as depicted in SEQ ID No. 7) is fused at its amino terminus to six histidine residues which serve to enable the polypeptide, once expressed from the host cell, to be isolated and purified by affinity chromatography using a Ni-chelate resin.

A flanking purification domain may be separated from the ERG8 polypeptide by a cleavage sequence such as that recognised by thrombin or Factor Xa so as to facilitate release of the polypeptide from the flanking sequence which may or may not be attached to an immobilised support. Alternatively, cyanogen bromide which cleaves at methionine residues can be employed to release the desired polypeptide from its flanking sequence.

The polypeptides of the invention can be synthesised chemically. For example, by the Merryfield technique (J. Amer. Chem. Soc. 85:2149–2154, 1968). Numerous automated polypeptide synthesisers, such as Applied Biosystems 431A Peptide Synthesizer also now exist. Alternatively, and preferably, the polypeptides of the invention are produced from a nucleotide sequence encoding the polypeptide using recombinant expression technology.

In a further aspect of the invention there are provided isolated polynucleotides (including genomic DNA, genomic RNA, cDNA and mRNA; double stranded as well as +ve and −ve strands) which encode the polypeptides of the invention. Single stranded DNA molecules of all or part of the ERG8 gene either +ve or −ve strand, find use inter alia, as hybridisation probes or PCR amplification primers. The sense strand of the complete gene sequence of native ERG8 is depicted in FIG. 1 (SEQ ID No. 5) hereinafter. It will be appreciated that a polynucleotide of the invention may comprise any of the degenerate codes for a particular amino acid, including the use of rare codons. Indeed, when producing the polypeptide by recombinant expression in heterologous host strains, it may be desirable to adopt the codon usage (preference) of the host organism (Murray. N.A.R. 17:477–508, 1989).

Thus, according to a further aspect invention there is provided an isolated polynucleotide comprising nucleic acid encoding the amino acid sequence depicted in SEQ ID No. 7 or a variant thereof, such as one possessing at least 80% identity thereto.

The invention further comprises convenient fragments of any one of the above polynucleotide/nucleic acid sequences. Convenient fragments may be defined by restriction endonuclease digests of nucleic acid comprising the ERG8 gene sequence. Such fragments are useful inter alia, for expressing short polypeptides fragments of ERG8 protein of the invention as well as for use as hybridisation probes. The present invention also provides a polynucleotide probe comprising any one of the above sequences or fragments together with a convenient label or marker, preferably a non-radioactive label or marker. Following procedures well known in the art, the probes can be used to identify and isolate not only corresponding nucleic acid sequences (i.e C. albicans ERG8 gene sequences) but, if sufficiently homologous, can also be used to identify the analogous gene from other organisms using techniques well known to the person skilled in the art. Such sequences may be comprised in libraries, such as genomic or cDNA libraries. The present invention also provides RNA transcripts corresponding to any of the above C. albicans ERG8 sequences or fragments. RNA transcripts can be used to prepare a polypeptide of the invention by in vitro translation techniques according to known methods (Sambrook et al. "Molecular Cloning—A Laboratory Manual, second edition 1989"). The invention further comprises full-length or fragment lengths of ERG8 gene (coding sequence) flanked by non-coding sequence which may include natural or non-natural sequence containing restriction enzyme recognition sequence motifs. The incorporation of suitable restriction enzyme recognition sites either side of the ERG8 coding region, or indeed any polynucleotide sequence from ERG8, facilitates cloning of the ERG8 gene or polynucleotide sequence into a suitable vector. A suitable polynucleotide comprises a full length C. albicans ERG8 gene (encoding the polypeptide that starts with methionine at position 1 and terminates with the leucine that precedes the stop codon TAA at position 1299 of FIG. 1) flanked by unique HindIII (5'-end)-XhoI (3'-end) restriction sites. Examples of oligonucleotide primers which are suitable for use in PCR amplification of ERG8, and which incorporate useful restriction enzyme sites to facilitate cloning, are disclosed as SEQ ID Nos. 10 and 11. Nucleotide changes or mutations may be introduced into a polynucleotide sequence by de novo polynucleotide synthesis, by site directed mutagenesis using appropriately designed oligonucleotide primers or by any other convenient means know to the person skilled in the art.

For expression purposes, it may be advantageous to engineer a restriction site at the 5'-end which is also capable of reconstituting the native amino-terminal methionine of the protein. The cleavage recognition sequence for the Nco1 restriction enzyme not only includes a sequence that codes for methionine, but also one that is capable of retaining a functional Kozak consensus sequence, enabling the ERG8 gene to be cloned at the 3'-end of a suitable promoter element in an expression vector.

The polynucleotides can be synthesised chemically, or isolated by one of several approaches known to the person skilled in the art such as polymerase chain reaction (PCR) or ligase chain reaction (LCR) or by cloning from a genomic or cDNA library.

Once isolated or synthesised, a variety of expression vector/host systems may be used to express ERG8 coding sequences. These include, but are not limited to microorganisms such as bacteria expressed with plasmids, cosmids or bacteriophage; yeasts tranformed with expression vectors; insect cell systems transfected with baculovirus expression systems; plant cell systems transfected with plant virus expression systems, such as cauliflower mosaic virus; or mammalian cell systems (for example those transfected with adenoviral vectors); selection of the most appropriate system is a matter of choice.

Expression vectors usually include an origin of replication, a promoter, a translation initiation site, optionally a signal peptide, a polyadenylation site, and a transcription termination site. These vectors also usually contain one or more antibiotic resistance marker gene(s) for selection. As noted above, suitable expression vectors may be plasmids, cosmids or viruses such as phage or retroviruses. The coding sequence of the polypeptide is placed under the control of an appropriate promoter, control elements and transcription terminator so that the nucleic acid sequence encoding the polypeptide is transcribed into RNA in the host cell transformed or transfected by the expression vector construct. The coding sequence may or may not contain a signal peptide or leader sequence for secretion of the polypeptide out of the host cell. Expression and purification of the polypeptides of the invention can be easily performed using methods well known in the art (for example as described in Sambrook et al. "Molecular Cloning—A Laboratory Manual, second edition 1989").

The vectors containing the DNA coding for the ERG8 polypeptides of the invention can be introduced (i.e transformed or transfected) into E. coli, S. cerevisiae, Pichia pastoris or any other suitable host to facilitate their manipulation (i.e. for mutagenesis, cloning or expression). Performance of the invention is neither dependent on nor limited to any particular strain of host cell or vector; those suitable for use in the invention will be apparent to, and a matter of choice for, the person skilled in the art.

Host cells transformed or transfected with a vector containing an ERG8 nucleotide sequence may be cultured under conditions suitable for the expression and recovery of the encoded proteins from the cell culture. Such expressed proteins/polypeptides may be secreted into the culture medium or they may be contained intracellularly depending on the sequences used, i.e. whether or not suitable secretion signal sequences were present.

The full-length native isolated C. albicans ERG8 protein (PMK enzyme) of the present invention, or a functional variant thereof, is useful as a target in biochemical assays, particularly for use in identifying inhibitors of the enzyme. However, to provide sufficient enzyme for a biochemical assays (for example, for use in a high throughput screen for enzyme inhibitors) the enzyme has to be expressed at high levels and it has to be purified. Two major constraints impair ERG8 expression and purification: (i) ERG8 is not expressed at high levels from C. albicans, and (ii) expression and protein purification methodology is not well advanced for C. albicans.

We have now been able to overcome these problems by controlled over-expression of the C. albicans ERG8 in a strain of Saccharomyces cerevisiae. S. cerevisiae is a model system for expression and purification of recombinant proteins. Use of S. cerevisiae to express C. albicans ERG8 means that transformation, expression and purification methodology used to produce and isolate the ERG8 protein can follow published procedures. As stated above, the invention is not limited to use of S. cerevisiae as the host for expression of C. albicans ERG8.

According to a further aspect of the invention there is provided a host cell adapted to express C. albicans ERG8 polypeptide or a variant thereof. The yeast S. cerevisiae is the preferred host cell of choice. According to a further aspect of the invention there is provided a novel expression system for expression of the C. albicans ERG8 gene, which system comprises an S. cerevisiae host strain having the C. albicans ERG8 gene in place of the native ERG8 gene from S. cerevisiae, whereby the C. albicans ERG8 gene is expressed. Preferred S. cerevisiae strains include JK9-3Dα and its haploid segregants.

The C. albicans ERG8 gene is preferably over-expressed relative to the expression derived from its own promoter. This is conveniently achieved by replacing the C. albicans ERG8 promoter by a stronger and preferably inducible promoter such as the S. cerevisiae GAL1 promoter, alpha factor or alcohol oxidase (for reviews see Ausubel et al. "Current Protocols in Molecular Biology", John Wiley & Sons, New York.).

The novel expression system is conveniently prepared by transformation of a heterozygous ERG8 deletion strain of a convenient S. cerevisiae host by a suitable plasmid comprising the C. albicans ERG8 gene using methods well known in the art (Ito et al. J. Bacteriol. 153:163–168, 1983; Schiestl and Grietz, Current Genetics 16:339–346, 1989).

The plasmid comprising the C. albicans ERG8 represents a further aspect of the invention. Particularly suitable plasmids for expression of C. albicans ERG8 in S. cerevisiae include pYES2(Invitrogen) and plasmids derived from pYES2 carrying a native S. cerevisiae promoter such as the glyceraldehyde-3-dehydrogenase promoter.

The heterozygous ERG8 deletion strain of a diploid S. cerevisiae host is conveniently achieved by disruption preferably using an antibiotic resistance cassette such as the kanamycin resistance cassette described by Wach et al (Yeast. 10:1793–1808, 1994).

As described earlier, the C. albicans ERG8 enzyme may be used in biochemical assays to identify agents which modulate the activity of the enzyme. The design and implementation of such assays will be evident to the biochemist of ordinary skill. The enzyme may be used to turn over a convenient substrate whilst incorporating/losing a labelled component to define a test system. Test compounds are introduced into the test system and measurements made to determine their effect on enzyme activity. Such assays are useful to identify inhibitors of the enzyme which may then prove valuable as antifungal agents.

Thus, in a further aspect of the invention we provide the use of a C. albicans ERG-8 gene and/or C. albicans PMK enzyme in an assay to identify inhibitors of the enzyme. In particular, we provide their use in pharmaceutical or agrochemical research.

Thus, according to a further aspect of the invention there is provided a method of identifying compounds that modulate, preferably inhibit, the activity of phosphomevalonate kinase (PMK), comprising, contacting a test compound with a polypeptide of the invention and determining the effect that the test compound has on the activity of the polypeptide.

The PMK (ERG8) protein catalyses the conversion of phosphomevalonate+ATP to pyrophosphomevalonate+ADP. By way of non-limiting example, the activity of the ERG8 enzyme may be determined by (i) measuring the increase in ADP production, (ii) by following the loss of ATP, or (iii) by monitoring transfer of radioactive label (i.e $H^3$, $C^{14}$, $P^{32}$) into phosphomevalonate.

A suitable assay that measures ADP production involves coupling the ADP produced by the action of PMK on phosphomevalonate+ATP substrate with pyruvate kinase and phosphoenolpyruvate to form pyruvate and ATP. The pyruvate is then reduced to lactate with lactate dehydrogenase which converts NADH to NAD. The production of NAD (directly linked to ADP production indicative of PMK action) is conveniently measured by detecting the change in absorbance at 340 nm (NADH oxidation product). In this assay, test compounds that inhibit PMK activity are identified by determining the ability of a compound to inhibit PMK activity as assessed by a reduction in ADP production as gauged by a reduction in the production of NAD from NADH using pyruvate kinase and lactate dehydrogenase as coupling enzymes as described above. The person skilled in the art would be able to develop other assays for measuring PMK activity without inventive input.

ATP can be conveniently assayed using commercially available kits (i.e Boehringer Mannheim) to monitor luminescence resulting from oxidation of luciferin to luciferase (Ford et al. J. Biolumin. Chemilumin. 11:149–167, 1996).

A suitable reaction that measures the production of radioactively labelled phosphomevalonate involves incubation PMK enzyme with cofactors, substrate ATP and phosphomevalonate, one of which carries a radioactive label. After reaction, pyrophosphomevalonate can be resolved from unreacted substrate by high voltage electrophoresis at pH3.5 on 3MM paper and the amount of radioactivity incorporated into pyrophosphomevalonate can be measured by scintillation counting (Lee and O'Sullivan. J. Biol. Chem. 260: 13909–13915, 1985).

Any convenient test compound or library of test compounds may be used in conjunction with the test assay. Particular test compounds include low molecular weight chemical compounds (preferably with a molecular weight less than 1500 daltons) suitable as pharmaceutical or veterinary agents for human or animal use, or compounds for non-administered use such as cleaning/sterilising agents or for agricultural use.

The ERG8 enzyme of the invention, and convenient fragments thereof may be used to raise antibodies. Such antibodies have a number of uses which will be evident to the molecular biologist or immunologist of ordinary skill. Such uses include, but are not limited to, monitoring enzyme expression, development of assays to measure enzyme activity, precipitation or purification of the enzyme and as a diagnostic tool to detect *C. albicans*. Enzyme linked immunosorbant assays (ELISAs) are well known in the art and would be particularly suitable for detecting the ERG8 polypeptide or fragments thereof. Antibodies raised against the polypeptides of the invention may be polyclonal, obtained for example by injecting the polypeptide(s) into a selected mammal (i.e. rabbit, mouse, goat or horse), and later collecting the immunised serum from the animal, and treating this according to procedures known in the art. Depending on the host species, various adjuvants may be used to enhance the immunological response against the injected polypeptide. Suitable adjuvants include, but are not limited to Freud's, aluminium hydroxide and SAF. Antibodies may also be monoclonal antibodies produced by hybridoma cells, phage display libraries or other methodology. Monoclonal antibodies may be inter alia, human, rat or mouse derived. For the production of human monoclonal antibodies, hybridoma cells may be prepared by fusing spleen cells from an immunised animal, e.g. a mouse, with a tumour cell. Appropriately secreting hybridoma cells may thereafter be selected (Koehler & Milstein. Nature. 256: 495–497, 1975; Cole et al. "Monoclonal antibodies and Cancer Therapy, Alan R Liss Inc, New York N.Y. pp 77–96). Rodent antibodies may be humanised using recombinant DNA technology according to techniques known in the art. Alternatively, chimeric antibodies, single chain antibodies, Fab fragments may also be developed against the polypeptides of the invention (Huse et al. Science. 256:1275–1281, 1989), using skills known in the art.

The polynucleotides and antibodies of the invention may be used in gene-probe or protein-probe methodologies, with or without amplification (for example, via PCR or second antibody detection) to detect or diagnose the presence of *C. albicans*. This is particularly valuable in diagnosing clinical infections. Accordingly, the invention provides diagnostic kits for the detection of *C. albicans* ERG8 or fragments thereof, and provides for the use of ERG8 protein, polypeptide fragments thereof and/or antibodies raised thereagainst as positive control. The reagents in the kit may be compartmentalised and the kit may also comprise instructions for use.

DNA diagnostics is based on DNA/RNA hybridisation technology, i.e. the specific in vitro binding of complementary single-stranded nucleic acid with the formation of double-stranded nucleic acid. The DNA/DNA or DNA/RNA double strands formed are termed hybrids. To detect the presence of *C. albicans* in a bodily fluid such as blood, total nucleic acid is isolated from the test fluid sample using standard techniques and the presence of *C. albicans* ERG8 nucleic acid in the sample is detected using for example detectably labelled probes comprising one or more of the polynucleotides of the invention. The probes can be short, chemically synthesised oligonucleotide probes of a length of approximately 10–50 nucleotides, or may be recombinantly expressed fragments of the ERG8 gene of approximately 0.3–1.5 Kb in size. Single stranded oligonucleotide probes which are specific for *C. albicans* are preferred. The probe can be provided with a suitable detectable reporter molecule label such as a radioisotope ($P^{32}$, tritium, $C^{14}$ or $S^{35}$), or a non-radioactive label such as digoxigenin or biotin, using techniques available to the person skilled in the art. Prior to the hybridisation reaction, all or any part of *C. albicans* ERG8 DNA containing the sequence to which the probe can hybridise, present in the test sample is amplified using for example PCR (polymerase chain reaction) or LCR (ligase chain reaction). For the specific hybridisation reaction, the test nucleic acid and if necessary the probe DNA is converted into single strands by denaturation (heat or alkali) and then very specifically hybridised with each other under stringent conditions. Under appropriate conditions the gene probe only hybridises to complementary sequences of the DNA or RNA to be detected. The hybridisation and detection assay can be carried out in a number of different formats known to the person skilled in the art including, solid-phase hybridisation of target DNA or probe coupled to a solid support such as nitrocellulose or magnetic beads. The hybridisation complex can then be determined quantitatively, following removal of unbound probe or test nucleic acid, by way of the reporter molecule label (e.g. fluorescent or radioactive) employed.

The test sensitivity of this single gene-probe diagnostic method can be increased by combination with DNA or RNA amplification techniques such as PCR or LCR. Using such amplification techniques, the DNA to be detected can be multipled by up to $10^9$.

There may only be 100–1000 organisms per ml of blood in association with *Candida* infections. Such small numbers of cells are easily detectable when combining the amplification and DNA-probe detection techniques offering the possibility of early detection of infection.

Thus, according to a further aspect of the invention there is provided a method of diagnosing the presence of the *C. albicans* ERG8 gene in a test sample, comprising: contacting a polynucleotide probe of at least 15 nucleotides in length, which probe is capable of specifically hybridising with the sequence depicted in SEQ ID No. 6, with the test sample under conditions which allow duplex formation between said polynucleotide probe and the nucleic acid in the test sample; and, detecting duplex formation. In a preferred embodiment the polynucleotide probe is detectably labelled. In another embodiment the polynucleotide probe is single stranded. In another embodiment the polynucleotide probe is completely complementary to the target sequence to be detected. According to a further aspect of the invention the polynucleotide probe is substituted for by a pair of oligonucleotide primers capable of specific PCR amplification of all or part of the ERG8 gene in the test sample, with subsequent identification of amplification product.

According to another aspect of the present invention there is provided a diagnostic kit for diagnosing or detecting the presence of *C. albicans* comprising, one or more diagnostic probe(s) and/or diagnostic primer(s) and/or antibodies capable of selectively hybridising or binding to the polynucleotide of SEQ ID No. 6 or the polypeptide of SEQ ID No. 7, or to variant sequences thereof as defined herein.

In a preferred embodiment, the diagnostic (detection) probes are provided on a microarray.

Such kits may further comprise appropriate buffer(s) and/or polymerase(s) such as thermostable polymerases, for example taq polymerase. They may also comprise companion/constant primers and/or control primers or probes. A companion/constant primer is one that is part of the pair of primers used to perform PCR. Such primer usually complements the template strand precisely.

In another embodiment the kit is an ELISA kit comprising one or more antibodies specific for the polypeptide depicted in SEQ ID No. 7, or a variant thereof as defined herein.

The following examples and figure describe and illustrate the invention. They are not intended to limit the scope of the invention in any way:

FIG. 1 shows the nucleotide sequence of the *C. albicans* gene encoding phosphomevalonate kinase. Translation start (ATG) and stop (TAA) codons are highlighted.

EXAMPLES

1. Cloning and Partial Sequence Determination of Two Separate Clones from a *Candida albicans* Genomic Library.

Two separate cloned and sequenced nucleic acid sequences from a *C. albicans* library (SEQ ID NOs. 1 & 3) were found to have homology to that of *S. cerevisiae* ERG8 gene. The complement of specific regions in SEQ ID Nos. 1 and 3 were synthesised as oligonucleotides (SEQ ID Nos. 2 & 4) for use in the isolation of a clone containing the *C. albicans* ERG8 gene.

2. Cloning and Sequence Determination of *Candida albicans* ERG8.

Using the two oligonucleotide primers (SEQ ID Nos. 2 and 4), the *C. albicans* ERG8 gene was isolated as a plasmid clone from a library of *C. albicans* genomic DNA in the yeast shuttle vector YEp24 using PCR. The *C. albicans* library was maintained in *E. coli* and independent bacterial colonies were grown in single wells of each of 15×384-well microtitre plates. The properties of the library plasmids are such that this gridded array contains approximately 2.5× the amount of DNA in the *C. albicans* genome.

Small aliquots of cells from each of the wells were mixed to produce a pool of cells that were derived from all of the wells from a single plate. Similar pools were made for all of the rows and all of the columns from each of the plates. Samples of each of the pools of the cells for each complete plate were used in PCR reactions with SEQ ID Nos. 2 and 4 oligonucleotide primers to identify plate(s) in the array carrying *C. albicans* ERG8. Subsequent PCR reactions with pools of cells from rows of wells and columns of wells defined the specific well(s) carrying a clone of *C. albicans* ERG8.

The PCR reactions contained in a total volume of 0.05 ml: 75 mM Tris-HCl (pH 8.8 at 25° C.), 20 mM $(NH_4)_2SO_4$, 1.5 mM $MgCl_2$, 0.01% Tween 20, 0.2 mM of each of dATP, dCTP, dGTP and dTTP, 1.25 units Taq DNA polymerase, 100 pmoles of each oligonucleotide primer and 0.005 ml *E. coli* cell suspension. PCR reactions were incubated at 94° C. for 1 min then for 30 cycles of the following: 94° C. for 1 min, 55° C. for 1 min, 72° C. for 1 min. PCR products were analysed by electrophoresis through agarose and visualised under UV light after staining with ethidium bromide.

Putative clones harbouring the ERG8 gene were selected, the plasmid DNAs in these clones were purified and the complete sequence of the *C. albicans* ERG8 gene was determined on both strands using flanking sequence- or insert sequence-specific oligonucleotide primers. The full-length of the *C. albicans* ERG8 gene, including 'start' ATG and 'stop' TAA is shown in FIG. 1. The protein translation of the gene is depicted in SEQ ID No. 7.

3. Generation of a Heterozygous ERG8 Deletion Strain of *S. cerevisiae*

Since PMK is an essential enzyme, only one allele of a diploid cell can be deleted without loss of viability. One ERG8 gene diploid strain of *S. cerevisiae* (JK9-3daa; Kunz et al., Cell 73:585–596 (1993)) was disrupted using a kanamycin resistance cassette as described by Wach et al. (Yeast 10:1793–1808, 1994) using the protocol described therein with the oligonucleotides shown in SEQ ID Nos. 8 and 9. Sporulation of the heterozygous diploid (ERG8/erg8::KanMX) yields only two viable spores that are both sensitive to kanamycin, showing ERG8 to be essential, and the characteristic arrest phenotype for the two inviable spores.

4. Complementation of a *S. cerevisiae* ERG8 Deletion with the Cloned *C. albicans* ERG8

The heterozygous ERG8/erg8::KanMX strain was transformed with the plasmid carrying the full-length *C. albicans* ERG8 gene within a fragment of *C. albicans* genomic DNA such that expression of the gene will depend on functionality of the *C. albicans* promoter in the heterologous *S. cerevisiae* host. Surprisingly, the gene carried on the plasmid failed to complement the gene deletion as demonstrated by a failure to recover kanamycin-resistant haploid cells after sporulation. This was probably due to inappropriate expression of *C. albicans* ERG8 in *S. cerevisiae*.

To enable expression of *C. albicans* ERG8 in *S. cerevisiae* and to facilitate purification of ERG8 protein as a result of over-expression in a suitable host, the *C. albicans* promoter was replaced by the efficient, inducible *S. cerevisiae* GAL1 promoter. The *C. albicans* ERG8 coding sequence was amplified by PCR using the oligonucleotides shown in SEQ ID Nos. 10 and 11, which contain convenient restriction enzyme sites for cloning the product of PCR into an appropriate expression vector such as pYES2 (Invitrogen). The identity of the PCR-amplified gene cloned into pYES2 was confirmed by DNA sequencing. After transformation into the heterozygous ERG8/erg8::KanMX strain, the plasmid was able to complement the erg8::KanMX allele in *S. cerevisiae* since kanamycin-resistant haploid spores were viable on medium containing galactose but not glucose. This *S. cerevisiae* strain is a useful source of biologically active *C. albicans* ERG8 protein for assays in vitro.

*C. albicans* ERG8 can also be conveniently overexpressed in bacteria such as *E. coli*. The *C. albicans* ERG8 coding sequence is amplified by PCR using oligonucleotides containing convenient restriction sites for cloning into expression vectors such as pT7#3.3. It is particularly convenient if the initiation codon for ERG8 is incorporated within one of the restriction sites. Oligonucleotides may also incorporate extra sequences to encode a small "tag" that aids the subsequent purification of the protein. Such tags include, for example, "His$_6$" tags which may be incorporated at the N- or C-terminus of ERG8. Recombinantly expressed tagged ERG8 protein can be conveniently purified by affinity chromatography purification methodology using commercially available purification kits (i.e Qiagen) (Borsig et al., Biochem. Biophys. Res. Commun. 240: 586–589).

5. Hybridisation Test of Nucleic Acid Variations of Specific Nucleic Acid Sequences 5.1 Hybridisation Test A method for detecting variant nucleic acids containing sequences related to specific ERG8 sequences such as natural alleles, is described. These variant nucleic acids may be present in a variety of forms such as within plasmids or other like vehicles which may be fixed on to a hybridisation membrane, such as a nitrocellulose or nylon filter ready for detection using a labelled probe. Hybridisation assays can also be performed to identify variant sequences from within genomic or cDNA libraries. Hybridisation technology is well advanced. It will be apparent to the person skilled in the art that the protocol described below is only one example of a hybridisation protocol suitable to identify ERG8 variant sequences.

5.2 Hybridisation Probe

Hybridisation probes may be generated from any fragment of DNA or RNA encoding the specific ERG8 nucleic sequence of interest. Such fragments can be for example, restriction fragments isolated following restriction enzyme digestion of nucleic acid containing the ERG8 nucleotide sequence or synthetic oligonucleotides specific for a region of the ERG8 gene or a complementary sequence thereto.

A hybridisation probe can be generated from a synthetic oligonucleotide or a dephosphorylated restriction fragment sequence by addition of a radioactive 5' phospate group from [$\gamma$-$^{32}$P]ATP by the action of T4 polynucleotide kinase. 20 pmoles of the oligonucleotide are added to a 20 µl reaction containing 100 mM Tris, pH7.5, 10 mM MgCl$_2$, 0.1 mM spermidine, 20 mM dithiothreitol (DTT), 7.55 µM ATP, 55 µCi [$\gamma$-$^{32}$P]ATP and 2.5u T4 polynucleotide kinase (Pharmacia Biotechnology Ltd, Uppsala, Sweden). The reaction is incubated for 30 minutes at 37° C. and then for 10 minutes at 70° C. prior to use in hybridisation. Methods for the generation of hybridisation probes from oligonucleotides or from DNA and RNA fragments (Chapters 11 and 10 respectively in Sambrook et al. ibid). A number of proprietary kits are also available for these procedures.

5.3 Hybridisation Conditions

Filters containing the nucleic acid are pre-hybridised in 100 ml of a solution containing 6×SSC, 0.1% SDS and 0.25% dried skimmed milk (Marvel™) at 65° C. for a minimum of 1 hour in a suitable enclosed vessel. A proprietary hybridisation apparatus such as model HB-1 (Techne Ltd) provides reproducible conditions for the experiment.

The pre-hybridisation solution is then replaced by 10 ml of a probe solution containing 6×SSC, 0.1% SDS, 0.25% dried skimmed milk (e.g. Marvel™) and the oligonucleotide probe generated above. The filters are incubated in this solution for 5 minutes at 65° C. before allowing the temperature to fall gradually to below 30° C. The probe solution is then discarded and the filters washed in 100 ml 6×SSC, 0.1% SDS at room temperature for 5 minutes. Further washes are then made in fresh batches of the same solution at 30° C. and then in 10° C. increments up to 60° C. for 5 minutes per wash.

After washing, the filters are dried and used to expose an X-ray film such as Hyperfilm™ MP (Amersham International) at −70° C. in a light-tight film cassette using a fast tungstate intensifying screen to enhance the photographic image. The film is exposed for a suitable period (normally overnight) before developing to reveal the photographic image of the radio-active areas on the filters. Related nucleic acid sequences are identified by the presence of a photographic image compared to totally unrelated sequences which should not produce an image. Generally, related sequences will appear positive at the highest wash temperature (60° C.). However, related sequences may only show positive at the lower wash temperatures (50, 40 or 30° C.).

These results will also depend upon the nature of the probe used. Longer nucleic acid fragment probes will need to be hybridised for longer periods at high temperature but may remain bound to related sequences at higher wash temperatures and/or at lower salt concentrations. Shorter, mixed or degenerate oligonucleotide probes may require less stringent washing conditions such as lower temperatures and/or higher Na$^+$ concentrations. A discussion of the considerations for hybridisation protocols is provided in Sambrook et al. (Chapter 11).

To prepare 20×SSC, 175.3 g of NaCl and 88.2 g of sodium citrate is dissolved in approximately 800 ml of water, the pH is adjusted to 7.0 using 10 N solution of NaOH and the volume is adjusted to 1 liter with water, before autoclaving.

What is claimed is:

1. A purified polypeptide having phosphomevalonate kinase (PMK) activity comprising the amino acid sequence depicted in SEQ ID No. 7.

2. The purified polypeptide having Phosphomevalonate kinase (PMK) activity of claim 1 wherein the polypeptide is (capable of isolation) isolated from *Candida albicans*.

3. A method to identify compounds that inhibit Phosphomevalonate kinase (PMK) activity, said method comprising the steps of contacting a test compound with the polypeptide of claim 1, in the presence of appropriate assay components and under conditions effective to detect inhibition of the (transfer of a phosphorous molecule from ATP to phosphomevalonate) PMK activity.

4. A diagnostic kit for detecting the presence of *Candida albicans* comprising (one or more antibodies capable of selectively binding to) an antibody that selectively binds to the polypeptide of claim 1.

* * * * *

UNITED STATES PATENT AND TRADEMARK OFFICE
CERTIFICATE OF CORRECTION

PATENT NO. : 7,001,757 B1
APPLICATION NO. : 10/069062
DATED : February 21, 2006
INVENTOR(S) : Rosamund et al.

It is certified that error appears in the above-identified patent and that said Letters Patent is hereby corrected as shown below:

On the title page: Item (75)
Please correct the first inventor's name to read: John David ROSAMOND.

In columns 23 and 24 amend the claims to read as follows:

2. The purified polypeptide having Phosphomevalonate kinase (PMK) activity of claim 1 wherein the polypeptide is isolated from *Candida albicans*.

3. A method to identify compounds that inhibit Phosphomevalonate kinase (PMK) activity, said method comprising the steps of contacting a test compound with the polypeptide of claim 1, in the presence of appropriate assay components and under conditions effective to detect inhibition of the PMK activity.

4. A diagnostic kit for detecting the presence of *Candida albicans* comprising an antibody that selectively binds to the polypeptide of claim 1.

Signed and Sealed this

Fourteenth Day of October, 2008

JON W. DUDAS
*Director of the United States Patent and Trademark Office*

SEQUENCE LISTING

<160> NUMBER OF SEQ ID NOS: 11

<210> SEQ ID NO 1
<211> LENGTH: 547
<212> TYPE: DNA
<213> ORGANISM: Candida albicans

<400> SEQUENCE: 1
ccaatggaaa aaggaaaagc cagaagaaag ctctgttgtg tatgaccagc ttaatagtgc        60
caatttacag tttatgaagg aattgaggga aatgcgtgaa aaatacgact cagacccaga       120

```
gacttatatt aaagagttag atcattctgt tgagcctttg actgttgcga ttaagaacat    180
cagaaaaggg ttacaagcat taacacaaaa atcagaggtt ccaattgaac ctgatgtcca    240
aacccagttg ttggaccgtt gtcaagagat tcctggttgt gttggcggtg tggttccagg    300
tgctggtgga tacgatgcaa tagctgtatt agtgttggaa aatcaagtgg gaaattttaa    360
gcagaaaact cttgaaaatc cagattattt tcataatgtt tactggttg atttggaaga     420 gcaaacagaa ggtgtacttg aagaaaaacc agaagactat ataggtttat aaaatatcac    480
taggatatgt ctacaaggtg atttcgatta gattttctgc tacccgtttt aacatatttt    540
acttcaa                                                              547

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:
      Single-stranded oligonucleotide

<400> SEQUENCE: 2
gctggtggat acgatgcaat a                                               21

<210> SEQ ID NO 3
<211> LENGTH: 577
<212> TYPE: DNA
<213> ORGANISM: Candida albicans
<220> FEATURE:
<221> NAME/KEY: misc_feature
<222> LOCATION: (1)..(577)
<223> OTHER INFORMATION: n can be a or g or c or t

<400> SEQUENCE: 3
atgtacatct ttcatgtttg aattcccagt tacttgcaat caatttttc aactctgtgg      60 ggaacttctc aggatcactt tctagaacct gaaacacgtc atttatcaaa gctggctgaa    120
atcttctata tacaatcaga ccataaattg cagttgcaac atcaaaccca gatcctatct    180 tttttgggc ataacaatgt gcaatctgtg caacgttgtg caaatatct ttattcgtac      240 tgataacatt ggggataaaa tgggataata aacttgtggc aacaactgac actaatcctg    300
ccgatgaacc taatccggtc ttttccactt cggtaatggc acgagaatgg taagaaaag     360 ttttttctcc attcgaggat gtcttggttt cagtatcttc ttgtgaatga tatccagggt    420
ccgagtaaat aatgatttca agatcaaatg cttcggtcgg ttgaatataa gctaaaaacc    480
gatggatata gttgcctcta aaaatgggat ttatgcgtga ctgnacttct ttgggttttc    540
ngtaattgat gatatgtgat antcccattc cccggtt                             577

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:
      Single-stranded oligonucleotide

<400> SEQUENCE: 4
ggggataaaa tgggataata aactt                                           25

<210> SEQ ID NO 5
<211> LENGTH: 1763
<212> TYPE: DNA
<213> ORGANISM: Candida albicans
```

```
<400> SEQUENCE: 5
gtggaaaaaa aagacagaac agtagattcc aacttcagaa tattcattca gatctgaaca      60 tttcttttc  tccgatcatc aattggcaat gtcaaaagca tttagtgcac ctggaaaagc     120
atttcttgct ggtggatatt tggttcttga gccaatttat gatgcttatg tgacagcatt    180
gtcatcacga atgcatgcag ttataacacc aaaaggaacc agtttgaaag aatctagaat    240
caaaatttct tcaccccaat ttgcaaacgg agaatgggaa tatcacatat catcaaatac    300
agagaagccc agagaagttc agtcacgcat aaatccattt ttagaggcaa ctatattcat    360
cgttttagct tatattcaac cgaccgaagc atttgatctt gaaatcatca tttactcaga    420
ccctggatat cattcacaag aagatactga aaccaagaca tcctcgaatg gagaaaaaac    480
atttctttac cattctcgtg ccattaccga agtggaaaag accggattag gttcatcggc    540
aggattagtg tcagttgttg ccacaagttt attatcccat tttatcccca atgttatcag    600
tacgaataaa gatattttgc acaacgttgc acagattgca cattgttatg cccaaaaaaa    660
gataggatct gggtttgatg ttgcaactgc aatttatggt ctgattgtat atagaagatt    720
tcagccagct ttgataaatg acgtgtttca ggttctagaa agtgatcctg agaagttccc    780
cacagagttg aaaaaattga ttgaaagtaa ctgggaattc aaacatgaaa gatgtacatt    840
accatacgga atcaagttat taatgggtga cgtcaagggt ggctcagaaa cacccaaatt    900
ggtatcacga gtactccaat ggaaaaagga aaagccagaa gaaagctctg ttgtgtatga    960
ccagcttaat agtgccaatt tacagtttat gaaggaattg agggaaatgc gtgaaaaata   1020
cgactcagac ccagagactt atattaaaga gttagatcat tctgttgagc ctttgactgt   1080
tgcgattaag aacatcagaa aagggttaca agcattaaca caaaaatcag aggttccaat   1140
tgaacctgat gtccaaaccc agttgttgga ccgttgtcaa gagattcctg ttgtgttgg    1200 tggtgtggtt ccaggtgctg gtggatacga tgcaatagct gtattagtgt tggaaaatca   1260
agtgggaaat tttaagcaga aaactcttga aaatccagat tattttcata atgtttactg   1320
ggttgatttg gaagagcaaa cagaaggtgt acttgaagaa aaaccagaag actatatagg   1380
tttataaaat atcactggga tatgtctaca aggtgttttc gattagagtt tttgatcccc   1440
attttaacat attttacttc aatcttacac tttatccttt taagtaggta tgtgtaggga   1500
aagagcctga tcttcataaa ccgttgcaaa ctaattgatt atattttcta ttgtaaattt   1560
catatgcagg aaatagctta ttcgacaaat tatttatttt cgtctcgttc tggtccaagt   1620
accccagaga cgaaataact gacaacacgc agggctgggt tggcattttc gtcacacgat   1680
tattattaat ggtaacaaaa aaggggrka  tgcccgtggt cgatacacaa atatttatga   1740
tatactttcc atatttttt  ttt                                           1763

<210> SEQ ID NO 6
<211> LENGTH: 1299
<212> TYPE: DNA
<213> ORGANISM: Candida albicans

<400> SEQUENCE: 6
atgtcaaaag catttagtgc acctggaaaa gcatttcttg ctggtggata tttggttctt      60
gagccaattt atgatgctta tgtgacagca ttgtcatcac gaatgcatgc agttataaca    120
ccaaaaggaa ccagtttgaa agaatctaga atcaaaattt cttcacccca atttgcaaac    180
ggagaatggg aatatcacat atcatcaaat acagagaagc cagagaagt  tcagtcacgc    240 ataaatccat ttttagaggc aactatattc atcgttttag cttatattca accgaccgaa    300
```

-continued

```
gcatttgatc ttgaaatcat catttactca gaccctggat atcattcaca agaagatact    360
gaaaccaaga catcctcgaa tggagaaaaa acatttcttt accattctcg tgccattacc    420
gaagtggaaa agaccggatt aggttcatcg gcaggattag tgtcagttgt tgccacaagt    480
ttattatccc attttatccc caatgttatc agtacgaata agatatttt gcacaacgtt    540 gcacagattg cacattgtta tgcccaaaaa aagataggat ctgggtttga tgttgcaact    600
gcaatttatg gtctgattgt atatagaaga tttcagccag ctttgataaa tgacgtgttt    660
caggttctag aaagtgatcc tgagaagttc cccacagagt tgaaaaaatt gattgaaagt    720
aactgggaat tcaaacatga aagatgtaca ttaccatacg gaatcaagtt attaatgggt    780
gacgtcaagg gtggctcaga acacccaaa ttggtatcac gagtactcca atggaaaaag    840
gaaaagccag aagaaagctc tgttgtgtat gaccagctta atagtgccaa tttacagttt    900
atgaaggaat tgagggaaat gcgtgaaaaa tacgactcag acccagagac ttatattaaa    960
gagttagatc attctgttga gcctttgact gttgcgatta agaacatcag aaaagggtta   1020
caagcattaa cacaaaaatc agaggttcca attgaacctg atgtccaaac ccagttgttg   1080
gaccgttgtc aagagattcc tggttgtgtt ggtggtgtgg ttccaggtgc tggtggatac   1140
gatgcaatag ctgtattagt gttggaaaat caagtgggaa attttaagca gaaaactctt   1200
gaaaatccag attattttca taatgtttac tgggttgatt tggaagagca aacagaaggt   1260
gtacttgaag aaaaaccaga agactatata ggtttataa                          1299
```

<210> SEQ ID NO 7
<211> LENGTH: 432
<212> TYPE: PRT
<213> ORGANISM: Candida albicans

<400> SEQUENCE: 7

```
Met Ser Lys Ala Phe Ser Ala Pro Gly Lys Ala Phe Leu Ala Gly Gly
  1               5                  10                  15

Tyr Leu Val Leu Glu Pro Ile Tyr Asp Ala Tyr Val Thr Ala Leu Ser
             20                  25                  30

Ser Arg Met His Ala Val Ile Thr Pro Lys Gly Thr Ser Leu Lys Glu
         35                  40                  45

Ser Arg Ile Lys Ile Ser Ser Pro Gln Phe Ala Asn Gly Glu Trp Glu
     50                  55                  60

Tyr His Ile Ser Ser Asn Thr Glu Lys Pro Arg Glu Val Gln Ser Arg
 65                  70                  75                  80

Ile Asn Pro Phe Leu Glu Ala Thr Ile Phe Ile Val Leu Ala Tyr Ile
                 85                  90                  95

Gln Pro Thr Glu Ala Phe Asp Leu Glu Ile Ile Tyr Ser Asp Pro
            100                 105                 110

Gly Tyr His Ser Gln Glu Asp Thr Glu Thr Lys Thr Ser Ser Asn Gly
        115                 120                 125

Glu Lys Thr Phe Leu Tyr His Ser Arg Ala Ile Thr Glu Val Glu Lys
    130                 135                 140

Thr Gly Leu Gly Ser Ser Ala Gly Leu Val Ser Val Ala Thr Ser
145                 150                 155                 160

Leu Leu Ser His Phe Ile Pro Asn Val Ile Ser Thr Asn Lys Asp Ile
                165                 170                 175

Leu His Asn Val Ala Gln Ile Ala His Cys Tyr Ala Gln Lys Lys Ile
            180                 185                 190
```

-continued

```
Gly Ser Gly Phe Asp Val Ala Thr Ala Ile Tyr Gly Leu Ile Val Tyr
        195                 200                 205

Arg Arg Phe Gln Pro Ala Leu Ile Asn Asp Val Phe Gln Val Leu Glu
    210                 215                 220

Ser Asp Pro Glu Lys Phe Pro Thr Glu Leu Lys Lys Leu Ile Glu Ser
225                 230                 235                 240

Asn Trp Glu Glu Lys His Glu Arg Cys Thr Leu Pro Tyr Gly Ile Lys
                245                 250                 255

Leu Leu Met Gly Asp Val Lys Gly Gly Ser Glu Thr Pro Lys Leu Val
            260                 265                 270

Ser Arg Val Leu Gln Trp Lys Lys Glu Lys Pro Glu Glu Ser Ser Val
        275                 280                 285

Val Tyr Asp Gln Leu Asn Ser Ala Asn Leu Gln Phe Met Lys Glu Leu
    290                 295                 300

Arg Glu Met Arg Glu Lys Tyr Asp Ser Asp Pro Glu Thr Tyr Ile Lys
305                 310                 315                 320

Glu Leu Asp His Ser Val Glu Pro Leu Thr Val Ala Ile Lys Asn Ile
                325                 330                 335

Arg Lys Gly Leu Gln Ala Leu Thr Gln Lys Ser Glu Val Pro Ile Glu
            340                 345                 350

Pro Asp Val Gln Thr Gln Leu Leu Asp Arg Cys Gln Glu Ile Pro Gly
        355                 360                 365

Cys Val Gly Gly Val Pro Gly Ala Gly Tyr Asp Ala Ile Ala
    370                 375                 380

Val Leu Val Leu Glu Asn Gln Val Gly Asn Phe Lys Gln Lys Thr Leu
385                 390                 395                 400

Glu Asn Pro Asp Tyr Phe His Asn Val Tyr Trp Val Asp Leu Glu Glu
                405                 410                 415

Gln Thr Glu Gly Val Leu Glu Glu Lys Pro Glu Asp Tyr Ile Gly Leu
            420                 425                 430
```

<210> SEQ ID NO 8
<211> LENGTH: 70
<212> TYPE: DNA
<213> ORGANISM: Artificial Sequence
<220> FEATURE:
<223> OTHER INFORMATION: Description of Artificial Sequence:
      Single-stranded oligonucleotide

<400> SEQUENCE: 8
aaatgtcaga gttgagagcc ttcagtgccc cagggaaagc gttactagct gcagctgaag    60
cttcgtacgc                                                          70

<210> SEQ ID NO 9
<211> LENGTH: 73
<212> TYPE: DNA
<213> ORGANISM: Artificial Sequence
<220> FEATURE:
<223> OTHER INFORMATION: Description of Artificial Sequence:
      Single-stranded oligonucleotide

<400> SEQUENCE: 9
agttatttat caagataagt ttccggatct ttttctttcc taacacccca ggcataggcc    60
actagtggat ctg                                                      73

```
-continued

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:
      Single-stranded oligonucleotide

<400> SEQUENCE: 10
cccaagcttg gcaatgtcaa aagcatttag tgc                                    33

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence:
      Single-stranded oligonucleotide

<400> SEQUENCE: 11
ccgctcgaga ttttataaac ctatatagtc ttctgg                                 36
```